Oct. 12, 1971 J. W. PATTERSON Plant Pat. 3,073
VARIETY OF ROSE
Filed Aug. 22, 1969
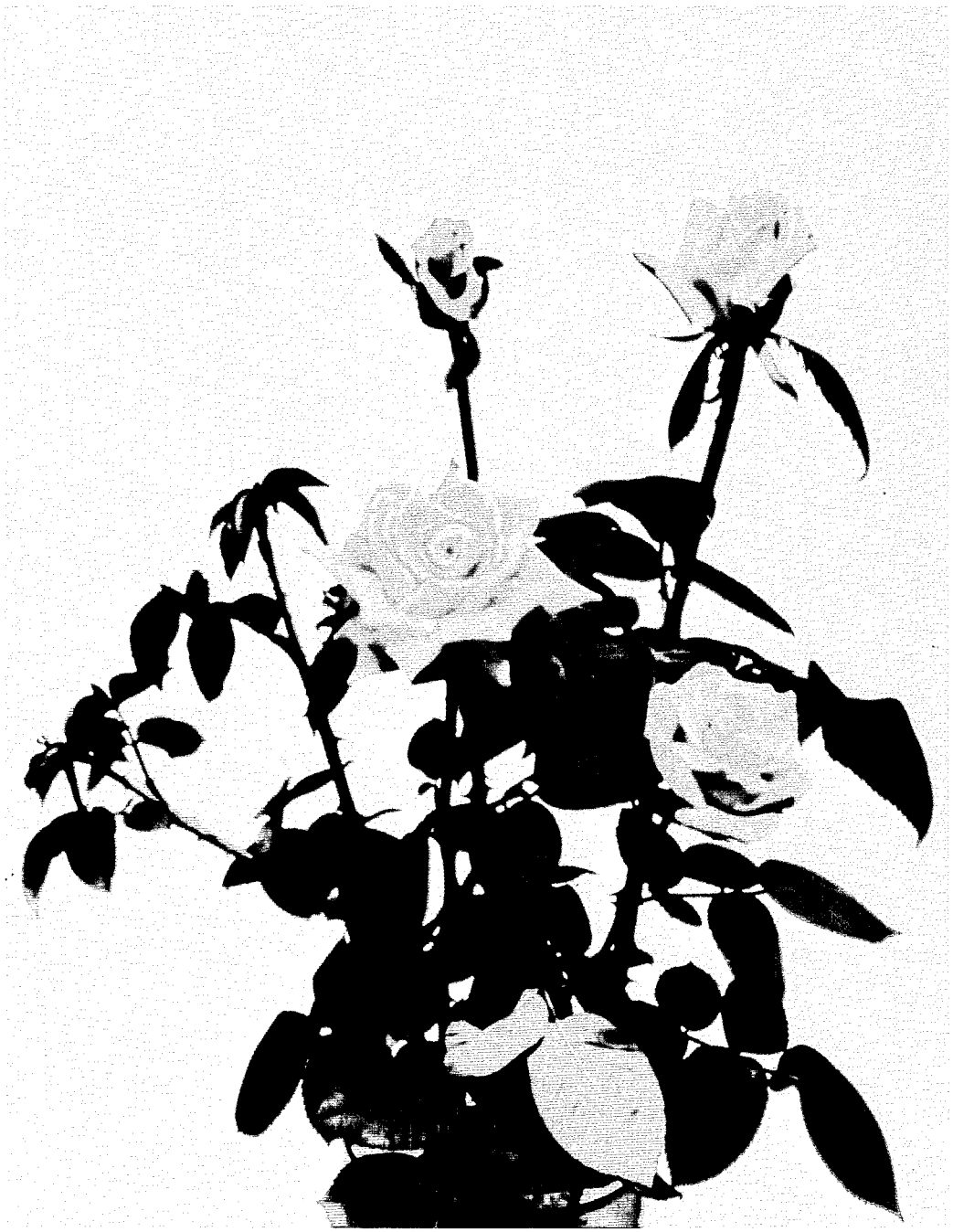

United States Patent Office

Plant Pat. 3,073
Patented Oct. 12, 1971

3,073
VARIETY OF ROSE

John W. Patterson, 6518 Kernel, Houston, Tex. 77017
Filed Aug. 22, 1969, Ser. No. 852,516
Int. Cl. A01h 5/00
U.S. Cl. Plt.—20 1 Claim The present invention relates to a new and distinct variety of rose plant of the hybrid tea class, which was originated by me by crossing the variety "Chrysler Imperial" (Plant Patent No. 1,167) with the variety "Happiness" (Plant Patent No. 911).

The primary object of this breeding was to produce a new rose variety which retains some of the better qualities of each variety used. One which retains the flower productivity and fragrance of the seed parent, "Chrysler Imperial," but which bears flowers of a distinct different shade of color of either parent, while at the same time retaining the long life of flowers as cut flowers and graceful long stems of the pollen parent "Happiness." It was also my purpose to achieve a new variety with great resistance to mildew and blackspot. These objectives were substantially achieved along with other desirable improvements, as evidenced by the following characteristics which are outstanding in the new variety and which distinguish it from its parents, as well as from all other varieties of which I am aware:

(1) Good strong growing habits;
(2) An abundance of large leathery green foliage;
(3) Relatively large flowers which are borne on long strong stems;
(4) Good flower fragrance;
(5) Good flower form;
(6) Average disease resistance with respect to mildew and blackspot when grown under comparable cultural conditions at Houston, Tex.;
(7) A distinctive attractive general color tonality of flowers corresponding to Current Red, Plate 821/1, in the newly open flowers, and to near Currant Red, Plate 821/3, in the three-day open flowers;
(8) Good keeping qualities of the flowers as cut flowers.

In comparison with its seed parent, "Chrysler Imperial," the new variety has more leathery foilage; has taller and stronger growing habits; flowers not quite as large nor as fragrant; and flower color is lighter shade of red.

As compared with the pollen parent, "Happiness," the new variety is a better and more vigorous grower and much better flower producer; is more disease resistant; and also has larger and more dense foilage.

A sexual reproduction of my new variety by butting as performed at Houston, Tex., and also by budding as performed at Wills Point, Tex., shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character. The illustrated blossom colors appear somewhat lighter due to the light reflection from the velvety petal surfaces.

The following is a detailed description of the new variety, with color terminology in accordance with the Horticultural Colour Chart of the Royal Horticultural Society, except where general color terms of ordinary dictionary significance are obvious.

Type: Bush; seedling.
Class: Hybrid tea
Breeding: Seedling.
*Seed parent.*—"Chrysler Imperial."
*Pollen parent.*—"Happiness."
Propagation: Holds its distinguishing characteristics through succeeding budding.
The cultivar name is "Los Tejas."

*Flower*

Locality where grown and observed: Houston, Tex.
Flowers borne: Singly to stem; on strong stems of long length.
Quantity of bloom: Abundant, outdoors.
Continuity: Continuous through growing season.
Fragrance: Moderate. Nature—tea.
Bud:
*Peduncle.*—Long; medium diameter; strong; erect; bark—smooth.
*Color.*—Scheeles Green, Plate 860, page 175.
*Thorns.*—None. Prickles and Hairs—few to many.
*Before calyx breaks.*—Size—medium large. Form—globular; some with foliaceous apendages on surface of bud extending beyond tip of the bud. Color—Scheeles Green, Plate 860/1, page 175, with foliaceous part slightly overlaid with Ruby Red, Plate 827/3, page 171.
*As calyx breaks.*—Color (outside of petal)—Cardinal Red, Plate 822, page 168.
*As first petal opens.*—Size—large. Form—globular. Color: Outside—base of petal Cardinal Red, Plate 822/3, page 168, changing to Cardinal Red, Plate 822/1, page 168; inside—near Currant Red, Plate 821/3 page 167.
*Opening.*—Opens up well outdoors; no unusual characteristics attributed to weather conditions.
Bloom:
*Size (when fully open).*—Medium to large; from 4½ to 5 inches.
*Petalage.*—Double; from 37 to 40 petals; arranged regularly.
*Form.*—Full and high—centered.
Petals:
*Texture.*—Thick; leathery. Inside and outside—velvety.
*Shape.*—Outer petals—ovate, with apex round. Intermediate petals—obovate, with apex near obtuse. Inner petals—obovate, with apex near obtuse. Edge of petals slightly ruffled in newly opened flowers. Petals slightly rolled under, some to a point in fully opened flowers.

This description of a newly opened flower was made from a rose grown outdoors during the month of June at Houston, Tex.

*Color.*—*Outer petal:* outside surface—near Rose Red, Plate 724/1, page 158; inside surface—base of petal Currant Red, Plate 821/3, page 167, remainder of petal changing to Cardinal Red, Plate 822/1, page 168. *Intermediate petal:* outside surface—Rose Red, Plate 724/2, page 158; inside surface—base of petal Currant Red, Plate 821/2, page 167, remainder of petal near Currant Red, Plate 821/1, page 167. *Inner petal:* outside surface—Rose Red, Plate 724/2, page 158; inside surface—near Currant Red, Plate 821/1, page 167.

This description was made from a rose that was open for three days outdoors during the month of June at Houston, Tex.:

*Color.—Outer petal:* outside surface—base Rose Red, Plate 724/3, page 158, remainder of petal near Currant Red, Plate 821/2, page 167; inside surface—Currant Red, Plate 821/2, page 167. *Intermediate petal:* outside surface—base of petal Rose Opal, Plate 022/1, page 110, changing to near Currant Red, Plate 821/1, page 167; inside surface—near Currant Red, Plate 821, page 167. *Inner petal:* outside surface—China Rose, Plate 024, page 111; inside surface—near Rose Opal, Plate 022, page 110.

*General color effect.*—Newly opened flower—near Currant Red, Plate 821/1. Three days open—near Currant Red, Plate 821/3, page 167.

*Behavior of petals.*—Drops off cleanly; no unusual characteristics attributed to weather conditions.

*Flower longevity.*—Cut roses grown outdoors and kept at living room temperatures—from four to six days in June. Show roses kept in refrigerator from eight to ten days before exhibited.

*Reproductive organs*

Stamens: Many; arranged regularly about pistils.

Filaments: Some short and some long length; most with anthers. Color—Spanish Orange, Plate 010/3, page 103.

Anthers: Medium large; all open at once. Color—near China Rose, Plate 024 to Plate 024/1, page 111.

Pollen: Sparse. Color—Cadmium Orange, Plate 8/2, page 8.

Pistils: Many.

Styles: Uneven; medium to short length; bunched. Color—Lemon Yellow, Plate 4/3, page 4.

Stigma: Color—near Vermilion, Plate 18/2, page 18.

Ovularies: Most enclosed in receptacle.

Hips: Few.

Sepals: Permanent; long length; spear-shaped. Color: Inside—Lettuce Green, Plage 861/1, page 176, overlaid with white fuzz; outside—Lettuce Green, Plate 861, page 176.

Seeds: Average amount.

*Plant*

Foliage:

*Leaves.*—Compound of five leaflets; Abundant; large size; heavy, leathery and slightly wrinkled.

*Leaflets.*—Shape—ovate. Apex—acute. Base—round. Margin—serrate.

*Color.*—Mature: Upper surface—near Spinach Green, Plate 0960, page 187; under surface—near Spinach Green, Plate 0960/2, page 187. Young: Upper surface—near Scheeles Green, Plate 860, page 175, very slightly overlaid with Erythrite Red, Plate 0027, page 190; under surface—near Scheeles Green, Plate 860/2, page 175, overlaid with Violet Purple, Plate 733/1, page 161.

*Rachis (the supporting stem of the compound leaf).*—Heavy. Upper side—heavily grooved. Under side—smooth surface; with thorns.

*Stipules.*—Long length; narrow; with points turning out at an angle about 45°.

Growth:

*Habit.*—Bush; upright.

*Growth.*—Free; very vigorous.

*Canes.*—Large.

*Main stems.*—Color—Spinach Green, Plate 0960/1, page 187, overlaid with streaks of near Garnet Brown, Plate 00918/3, page 192. *Thorns*—many; medium to long length; some slightly hooked downward; with broad thick base; very sharp points; color—near Garnet Brown, Plate 00918, page 192. *Prickles*—Few. *Hairs*—None.

*Branches.*—Color—Scheeles Green, Plate 860, page 175. Thorns—many; medium to long length; most with straight sharp points, few hooked downward; wide base; color—near Erythrite Red, Plage 0027, page 190. *Prickles*—several.

*New Shoots.*—Color—Scheeles Green, Plate 860/1, page 175. *Thorns*—many; medium length; some straight, some hooked downward; color—Lettuce Green, Plate 861, page 176. *Prickles*—few.

I claim:

1. A new and distinct variety of rose plant of the hybrid tea class, substantially as herein shown and described, characterized particularly as to novelty by the unique combination of vigorous growing and good flower producing habits, profuse leathery green foliage, relatively large flowers which are borne on strong stems of long length, good flower form, good flower fragrance, average disease resistance, a distinctive and attractive general color tonality of the flowers corresponding to Currant Red, Plate 821/1, in the newly open flowers, and to near Currant Red, Plate 821/3, in the three-days open flowers, and good keeping qualities of the flowers as cut flowers.

No references cited.

ROBERT E. BAGWILL, Primary Examiner